United States Patent
Kanz et al.

(10) Patent No.: US 6,596,005 B1
(45) Date of Patent: Jul. 22, 2003

(54) STEERABLE ABLATION BURR

(75) Inventors: Bill Kanz, Sacramento, CA (US); Denise Drummond, North Ogden, UT (US); Robert Barry, Kirkland, WA (US); Paul A. Hirst, Liberty Lake, WA (US); Mark Wyzgala, Bellevue, WA (US); Gary Swinford, Issaquah, WA (US); Edward Wulfman, Woodinville, WA (US); Tom Clement, Redmond, WA (US); Tom Kadavy, Bellevue, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 100 days.

(21) Appl. No.: 09/670,416

(22) Filed: Sep. 26, 2000

Related U.S. Application Data

(62) Division of application No. 09/262,502, filed on Mar. 4, 1999, now Pat. No. 6,146,395.
(60) Provisional application No. 60/076,963, filed on Mar. 5, 1998.

(51) Int. Cl.[7] ................................. A61D 1/02
(52) U.S. Cl. ...................... 606/159; 606/170
(58) Field of Search ............... 606/1, 159, 170, 606/171, 180, 108, 194; 604/22, 96, 523, 49, 95.04

(56) References Cited

U.S. PATENT DOCUMENTS

| | | | |
|---|---|---|---|
| 3,058,473 A | * | 10/1962 | Whitehead ............... 604/95.04 |
| 3,320,957 A | | 5/1967 | Sokolik |
| 3,996,938 A | | 12/1976 | Clark, III |
| 4,273,128 A | | 6/1981 | Lary |
| 4,445,509 A | | 5/1984 | Auth |
| 4,627,436 A | | 12/1986 | Leckrone |
| 4,650,466 A | | 3/1987 | Luther |
| 4,685,458 A | | 8/1987 | Leckrone |
| 4,850,957 A | | 7/1989 | Summers |
| 4,886,490 A | | 12/1989 | Shiber |
| 4,924,863 A | | 5/1990 | Sterzer |
| 4,926,858 A | | 5/1990 | Gifford, III et al. |
| 5,030,201 A | | 7/1991 | Palestrant |
| 5,034,001 A | | 7/1991 | Garrison et al. |
| 5,071,424 A | | 12/1991 | Reger |
| 5,074,871 A | | 12/1991 | Groshong |
| 5,087,265 A | | 2/1992 | Summers |
| 5,176,126 A | * | 1/1993 | Chikama .................. 604/95.04 |
| 5,304,199 A | | 4/1994 | Myers |
| 5,312,427 A | | 5/1994 | Shturman |
| 5,372,587 A | * | 12/1994 | Hammerslag et al. ... 604/95.04 |
| 5,554,163 A | | 9/1996 | Shturman |
| 5,656,029 A | * | 8/1997 | Imran et al. ............. 604/95.04 |
| 5,749,883 A | | 5/1998 | Halpern |
| 5,766,192 A | | 6/1998 | Zacca |
| 5,843,103 A | | 12/1998 | Wulfman |
| 5,897,566 A | | 4/1999 | Shturman et al. |

\* cited by examiner

Primary Examiner—Michael J. Milano
Assistant Examiner—Jessica R Baxter
(74) Attorney, Agent, or Firm—Christensen O'Connor Johnson Kindness PLLC

(57) ABSTRACT

A catheter including an elongate drive shaft having a proximal end and a distal end, an ablation burr disposed at the distal end expandable between a first position and a second position, wherein in the second position has a greater transverse dimension than in the first position. The catheter of the present invention can include a mechanism for positioning the burr eccentrically within a vessel lumen. In this context, expansion means that the burr can ablate a lumen having a larger diameter than the diameter of the lumen of the guide catheter to which the device is advanced.

6 Claims, 6 Drawing Sheets

STEERABLE ABLATION BURR

RELATED APPLICATIONS

This application is a divisional of prior application Ser. No. 09/262,502, filed Mar. 4, 1999, now U.S. Pat. No. 6,146,395 which in turn claims the benefit of U.S. Provisional Application No. 60/076,963, filed Mar. 5, 1999, the priority of which is hereby claimed under 35 U.S.C. §119 and 120.

BACKGROUND OF THE INVENTION

The present invention generally relates to constructions for intravascular treatment devices useful for removing vascular occlusion material from a vascular occlusion or from a vascular lumen. The invention more specifically relates to "expandable" intravascular occlusion material removal devices, as well as to methods of using those devices to treat vascular diseases. In this context, "expandable" means that the burr can ablate a lumen having a larger diameter than the diameter of the lumen of the guide catheter to which the burr is advanced.

Vascular diseases, such as atherosclerosis and the like, have become quite prevalent in the modem day. These diseases may present themselves in a number of forms. Each form of vascular disease may require a different method of treatment to reduce or cure the harmful effects of the disease. Vascular diseases, for example, may take the form of deposits or growths in a patient's vasculature which may restrict, in the case of a partial occlusion, or stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies are being developed. While a number of invasive therapies are available, it is desirable to develop non-invasive therapies as well. Minimally invasive therapies may be less risky than invasive ones, and may be more welcomed by the patient because of the possibility of decreased chances of infection, reduced post-operative pain, and less post-operative rehabilitation. One type of non-invasive therapy for vascular diseases is pharmaceutical in nature. Clot-busting drugs have been employed to help break up blood clots which may be blocking a particular vascular lumen. Other drug therapies are also available. Further, minimally invasive intravascular treatments exist that are not only pharmaceutical, but also revascularize blood vessels or lumens by mechanical means. Two examples of such intravascular therapies are balloon angioplasty and atherectomy which physically revascularize a portion of a patient's vasculature.

Balloon angioplasty comprises a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and then is inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It is to be noted, however, that this procedure does not remove the occluding matter from the patient's vasculature, but displaces it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus are not prone or susceptible to angioplastic treatment. Even if angioplasty is successful, thereby revascularizing the vessel and substantially restoring normal blood flow therethrough, there is a chance that the occlusion may recur. Recurrence of an occlusion may require repeated or alternative treatments given at the same intravascular site.

Accordingly, attempts have been made to develop other alternative mechanical methods of minimally invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty and/or drug therapies.

One such alternative mechanical treatment method involves removal, not displacement, as is the case with balloon angioplasty, of the material occluding a vascular lumen. Such treatment devices, sometimes referred to as atherectomy devices, use a variety of means, such as lasers, and rotating cutters or ablaters, for example, to remove the occluding material. The rotating cutters may be particularly useful in removing certain vascular occlusions. Since vascular occlusions may have different compositions and morphology or shape, a given removal or cutting element may not be suitable for removal of a certain occlusion.

Alternatively, if a patient has multiple occlusions in his vasculature, a given removal element may be suitable for removing only one of the occlusions. Suitability of a particular cutting element may be determined by, for example, its size or shape. Thus, a treating physician may have to use a plurality of different treatment devices to provide the patient with complete treatment. This type of procedure can be quite expensive because multiple pieces of equipment may need to be used (such intravascular devices are not reusable because they are inserted directly into the blood stream), and may be tedious to perform because multiple pieces of equipment must be navigated through an often-tortuous vascular path to the treatment site.

SUMMARY OF THE INVENTION

The present invention pertains generally to devices for performing atherectomy. In particular, various embodiments of an atherectomy device are disclosed which can ablate a lumen having a larger diameter than the diameter of the lumen of the guide catheter through which the device is advanced.

In one embodiment, an elongate shaft is provided having a proximal and a distal end. The shaft defines a lumen. A burr deflector is disposed at the distal end of the shaft. The burr deflector includes a burr engaging surface. An elongate rotatable drive shaft extends through the lumen of the first shaft. The drive shaft has a proximal end and a distal end. A burr is disposed at the distal end of the drive shaft. The drive shaft and burr are shiftable relative to the burr deflector. The drive shaft and burr may be shifted between a first position and a second position, wherein the burr is transversely shifted relative to the burr deflector. Preferably, the deflection is co-linear to the length of the drive shaft.

The burr engaging surface is preferably disposed at an acute angle to the length of the first shaft. The burr preferably includes an engaging surface disposed at an acute angle relative to the drive shaft such that the engaging surfaces provide a path along which the burr can shift transversely relative to the burr deflector.

In yet another embodiment of a device in accordance with the present invention an elongate shaft is provided which has a proximal and a distal end. The shaft defines a lumen. An elongate rotatable drive shaft extends through the lumen. The drive shaft has a proximal end and a distal end. A burr is disposed at the distal end of the drive shaft. A bushing is disposed around the drive shaft proximate the burr. A steering line is connected to the bushing. The steering line can be pulled by an operator to shift the bushing and thus the burr and drive transversely.

In yet another embodiment of a device in accordance with the present invention, an elongate rotatable drive shaft is provided having a proximal and a distal end. An ablation burr is disposed at the distal end of the drive shaft. The ablation burr includes a mechanism which expands transversely in response to the centrifugal force generated when the burr rotates.

In one embodiment, the mechanism is generally tubular and has a proximal end and a distal end constrained against expansion. The central portion of the tubular member is allowed to expand under the influence of the centrifugal force. In yet another embodiment of the mechanism, a member having a generally helical cross-section is provided which tends to unwind, increasing its transverse diameter as the burr rotates. In yet another embodiment of the mechanism, a line is provided having a proximal end and a distal end. The ends of the line are held a distance apart less than the length of the line. An abrasive is disposed on the line. As the burr is rotated, the line moves transversely. In yet another embodiment of the mechanism includes a plurality of bristles which can shift transversely under the influence of centrifugal force.

In another embodiment of the atherectomy device in accordance with the present invention, an elongate rotatable drive shaft is provided having a proximal end and a distal end. A lumen is defined through the elongate drive shaft. A balloon including an outer surface and defining a balloon enclosure in fluid communication with the inflation lumen is disposed at the distal end of the drive shaft. An abrasive is disposed on the outer surface of the balloon. The balloon can be dilated by pressure or centrifugal force to increase the transverse dimension of the abrasive surface.

In yet another embodiment of an atherectomy device in accordance with the present invention, an elongate shaft is provided having a proximal end and a distal end. The shaft defines a drive shaft lumen and an inflation lumen. A rotatable drive shaft, having a proximal end and a distal end, is disposed in the drive shaft lumen. An ablating burr is disposed at the distal end of the drive shaft. A balloon is disposed eccentrically on the drive shaft proximate the burr. The balloon can be inflated to push against the vessel wall and shift the drive shaft and burr transversely within the vessel lumen.

In yet another embodiment of an atherectomy device in accordance with the present invention, an elongate rotatable drive shaft is provided having a proximal end and a distal end. An ablation burr is eccentrically connected to the drive shaft at the distal end of the shaft. A counterweight is disposed on the burr to place the center of mass of the burr in line with the longitudinal axis of the drive shaft. The presence of the counterweight dampens whipping of the burr which might otherwise occur during rotation of the drive shaft. This embodiment is related to that disclosed in U.S. patent application Ser. No. 08/987,969, filed Dec. 10, 1997 and entitled ASYMMETRIC BURRS FOR ROTATIONAL ABLATION incorporated herein by reference.

In yet another embodiment of the atherectomy device in accordance with the present invention, an elongate shaft is provided having a proximal end and a distal end. The shaft defines a lumen therethrough. A rotatable drive shaft having a proximal end and a distal end, is disposed through the lumen. A burr, including a plurality of spring members is disposed at the distal end of the drive. The drive shaft and the burr are shiftable between a first position and a second position. In the first position, the spring members are disposed at least in part within the lumen of the first shaft and are transversely constrained thereby. In the second position, the spring members are transversely restrained less than in the first position such that the burr has a greater transverse dimension in the second position than in the first position.

In yet another embodiment of an atherectomy device in accordance with the present invention, an elongate rotatable drive shaft is provided having a proximal end and a distal end, the drive shaft includes a generally helical-shaped portion proximate the distal end biased to expand when unconstrained. An abrasive is disposed on the helical portion. The helical portion can be advanced to the site where atherectomy will be performed in a constrained and collapsed state through a guide catheter. When the helical shaped portion exits the guide catheter, the helically shaped portion, then unconstrained, will expand transversely.

DETAILED DESCRIPTION OF THE INVENTION

Figure 1:
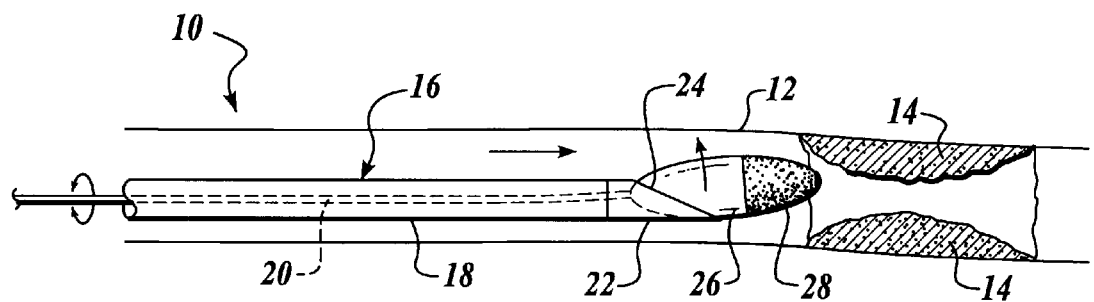
FIG. 1 is a side view of a catheter assembly in accordance with the present invention.

Referring now to the drawings, wherein like reference numerals refer to like reference elements throughout the several views, FIG. 1 is a side view of catheter 10 in accordance with the present invention. As shown in FIG. 1, catheter 10 is disposed within vessel 12 proximate a plaque deposit 14. Catheter 10 includes an elongate shaft 16. Shaft 16 includes an outer shaft 18 having a proximal end a distal end and defining a drive shaft lumen therethrough. Catheter 16 also includes a drive shaft 20 having a proximal end a distal end and extending through outer shaft 18. Disposed at the distal end of outer shaft 18 is a burr deflector 22 having a burr engaging surface 24. Disposed at the distal end of drive shaft 20 is a burr 26 rotatable by drive shaft 20, and including an abrasive surface 28.

As will be appreciated by those skilled in the art, suitable manifold and motor can be provided at the proximal end of catheter 10 to rotate burr 26 and facilitate the uses of catheter 10 as herein described. Those skilled in the art will appreciate the various biocompatible materials available to construct catheter 10 including burr 26. This is also true with respect to the various embodiments of the catheters discussed below. Those skilled in the art will recognize the various manifold, motor, infusion displays control mechanisms and other devices that can advantageously be connected to the proximal ends of the catheter to facilitate their use. Additionally, those skilled in the art will recognize various biocompatible materials, and methods available to construct each embodiment.

In use, catheter 10 is advanced percutaneously to a coronary lesion including plaque 14. Burr 26 is advanced to plaque as shown by the arrow parallel to shaft 16. Burr 26 is then rotated by drive shaft 26 as shown by the arrows such that plaque deposit 14 is grounded to micro fine particles. Catheter 10 can be advanced to the lesion through a guide catheter (not shown) having an inner lumen at least slightly greater in diameter than the diameter of burr 26.

As shown in FIG. 1, the inside diameter of vessel 12 is greater than the diameter of burr 26. In order for burr 26 to be positioned within vessel 12 to remove plaque 14, shaft 10 can be drawn proximally to engage burr 26 against burr deflector surface 24. As burr 26 is forced into surface 24 it will tend to slide proximally along surface 24 while simultaneously being displaced transversely as shown by the arrow on burr 26. The greater the transverse dimension of surface 24, the greater is the possible transverse movement of burr 26. The transverse movement of burr 26 is preferably co-linear with the length of the drive shaft.

Figure 2:
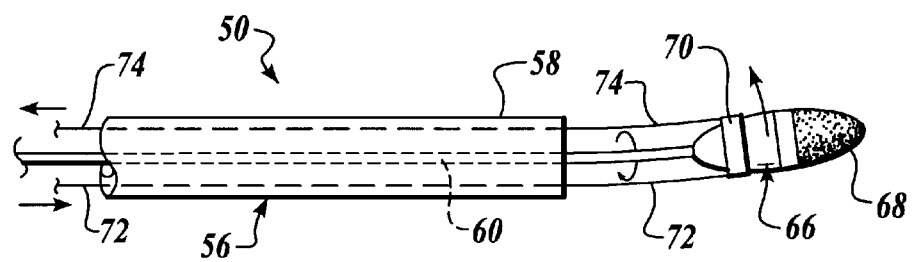
FIG. 2 is a side view of another embodiment of a catheter in accordance with the present invention.

FIG. 2 is a view of an alternate embodiment of an atherectomy catheter 50 in accordance with the present invention. Catheter 50 includes an elongate shaft 56 including an outer shaft 58 defining a drive shaft lumen therethrough. A drive shaft 60 extends through the lumen. Drive shaft 60 includes a proximal end and a distal end. Disposed at the distal end of drive shaft 60 is a burr 66 having an abrasive coating 68. Disposed around a proximal portion of burr 66 is a bushing 70. Bushing 70 can include an inwardly disposed circumferential flange which engages a circumferential groove (not shown) in burr 66 such that bushing 70 is fixedly connected to burr 66, yet burr 66 can rotate within bushing 70. Connected to opposite sides of bushing 70 and extending proximally through shaft 58 are steering wires 72 and 74.

Catheter 50 can be used as described above with respect to catheter 10. Unlike catheter 10, however, rather than having a burr deflector 22 to transversely move burr 26, burr 60 can be shifted from side to side by pulling proximally a steering wire 72 or 74. Pulling steering wire 74 proximally as steering wire 72 is allowed to move distally will shift burr 66 transversely toward wire 74 as shown by the arrow on burr 66. Similarly, burr 66 can be shifted transversely in the opposite direction by pulling steering wire 72 proximally while allowing wires 74 to shift distally.

To perform an atherectomy procedure using catheter 50, catheter 50 can be advanced to percutaneously to the cite of the lesion through a guide catheter having an inside diameter at least slightly greater than the transverse diameter of burr 66. Burr 66 can be rotated as shown by the arrow proximate drive shaft 60 and be engaged with the lesion. Burr 66 can be moved transversely by steering wires 72 and 74 as necessary to remove the plaque.

Figure 3:
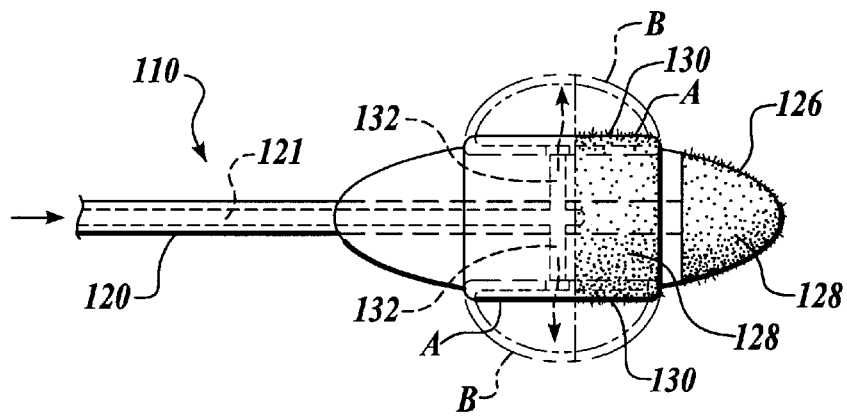
FIG. 3 is a side view of yet another embodiment of the catheter in accordance with the present invention.

FIG. 3 is a view of yet another embodiment of an atherectomy catheter 110 in accordance with the present invention. Catheter 110 includes an elongate drive shaft 120 having a proximal end and distal end. Drive shaft 120 defines a lumen 121 therethrough. Disposed at the distal end of drive shaft 120 is burr 126 having an abrasive coating 128. Burr 126 includes a generally tubularly shaped member 130 connected to burr 126 at the member's proximal and distal ends. Burr 126 includes lumens 132 in fluid communication with lumen 121 of shaft 120. Lumens 132 lead from lumen 121 to the inside surface of member 130.

In use, catheter 110 is advanced to a lesion as described above with respect to the other catheter embodiments. Rather than including a mechanism for transversely shifting a burr however, the tubular member 130 of burr 126 is sufficiently elastic to stretch transversely under the influence of centrifugal force when tip 126 is rotated by shaft 120. Rotation of tip 126, thus will move tubular member 130 from a first position A to a second position B. In second position B, burr 126 can ablate a larger diameter path. While member 130 is moving from position A to position B, fluid may be introduced through lumens 121 and 132 as shown by the arrows into the space created inside member 130.

Figure 4:
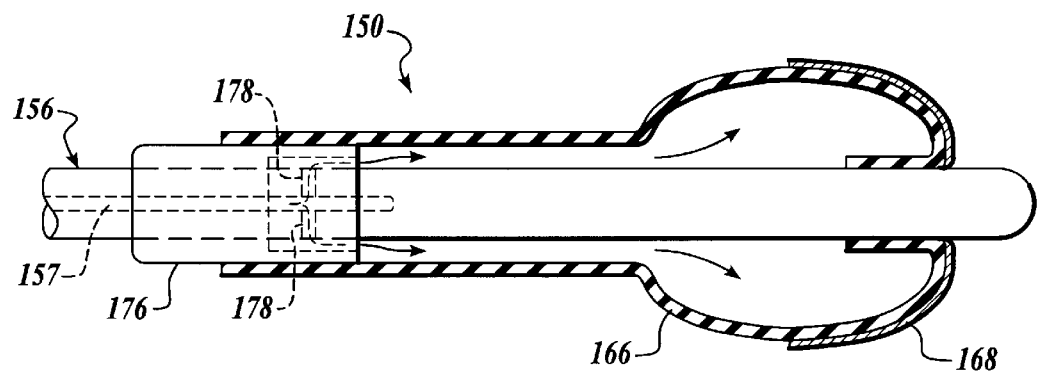
FIG. 4 is a longitudinal, cross-sectional view of yet another embodiment of the catheter in accordance with the present invention.

FIG. 4 is a cross-sectional view of yet another embodiment of a catheter 150 in accordance with the present invention. Catheter 150 includes an elongate shaft 156 defining an inflation lumen 157. Disposed proximate the proximal end of shaft 156 is a balloon 166 defining a burr having an abrasive coating 168. Catheter 150 can include a manifold 176 including lumens 178 in fluid communication with lumen 157 and the interior space of balloon 166.

In use, balloon 166 is advanced percutaneously to a lesion. At the lesion, balloon 166 is inflated to increase its diameter. Abrasive surface 168 is then advanced into engagement with the plaque. Balloon 166 is then rotated to abrade plaque.

Figure 5:
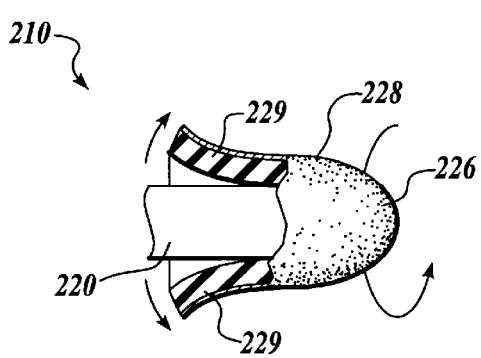
FIG. 5 is a fragmentary, cross-sectional view of yet another catheter in accordance with the present invention.

FIG. 5 is a partial, cross-sectional view of yet another embodiment of a catheter 210 in accordance with the present invention. Catheter 210 includes an elongate drive shaft 220 having a proximal end and a distal end. A burr 226 is disposed at the distal end of drive shaft 220. Burr 226 includes an abrasive coating 228 and a distal flexible portion or skirt 229 which is free to move generally transversely under the influence of centrifugal force as burr 226 is rotated by shaft 220. The arrows proximate skirt 229 show that the direction of the generally transverse movement of skirt 229 to increase the effective diameter of burr 226. The arrow proximate the distal end of burr 226 shows the rotation of burr 226. While burr 226 is not rotating skirt 229 can be disposed generally parallel to shaft 220 and then elastically stretch to the position shown in FIG. 5 when burr 226 is rotated.

Figure 6:
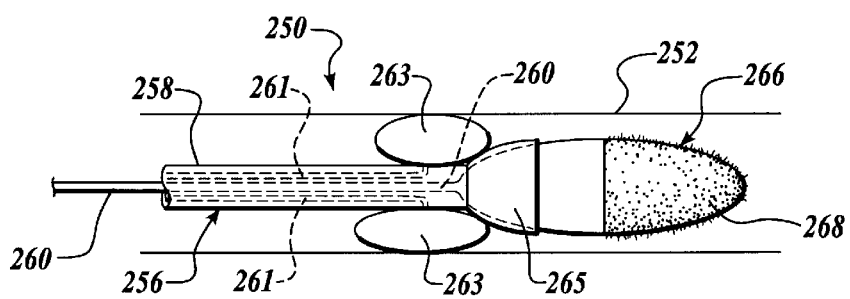
FIG. 6 is a side view of yet another embodiment of the catheter in accordance with the present invention.

FIG. 6 is a side view of yet another alternate embodiment of a catheter 250 in accordance with the present invention. Catheter 250 is shown disposed within a vessel lumen 252. Catheter 250 includes an elongate shaft 256 having a proximal end and a distal end. Catheter 256 includes an outer shaft 258 which defines the drive shaft lumen and two inflation lumens 261. An elongate drive shaft 260 is disposed through the drive shaft lumen. A cup shaped bearing 265 is disposed at the distal end of shaft 256. A burr 266 is connected to the distal end of drive shaft 260. The distal end of burr 266 can include an abrasive coating 268. The proximal end of burr 266 can be nested within bearing 265. Connected to shaft 258 proximate burr 266 are balloons 263. Balloons 263 define a balloon envelope in fluid communication with inflation lumens 261. Additional balloons may be used to increase the positional control of burr 266.

Catheter 250 is advanced as described above with respect to the alternate embodiments in accordance with the present invention to perform the atherectomy procedure. Likewise, burr 266 is rotated to abrade plaque. In order to shift burr 266 transversely within lumen 252, balloons 263 may be alternately inflated or deflated to engage the wall of vessel 252 forcing burr 266 transversely in a direction opposite the resultant force of balloons 263 incident the wall of vessel 252.

Figure 7:
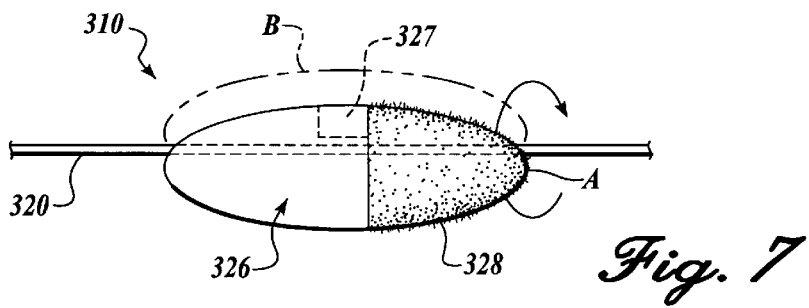
FIG. 7 is a side view of yet another embodiment of the catheter in accordance with the present invention.

FIG. 7 is a side view of yet another embodiment of a catheter 310 in accordance with the present invention. Catheter 310 includes an elongate shaft 320. Shaft 320 includes a proximal end and a distal end. A burr 326 is disposed eccentrically on shaft 320 proximate the distal end of shaft 320. Burr 326 includes an abrasive coating 328. A counterweight 327 is disposed in burr 326. The counterweight has a weight sufficient to shift the center of mass of burr 326 such that it lies generally on the longitudinal axis of shaft 320. The effect of counterweighting can also be achieved by an asymmetrical shaping of the burr and/or creating voids in the burr to shift the distribution of the burrs weight. This allows burr 326 to be rotated by shaft 320 through a position A and B as shown without whipping the distal end of shaft 322. By eccentrically mounting burr 326 on shaft 320 it can be appreciated by reference to positions A and B that a larger area can be circumscribed by the surface of burr 326 as burr 326 is rotated by shaft 320 than if the burr were rotated about its central axis.

Figure 8:
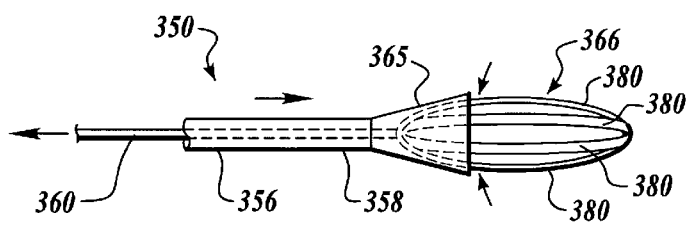
FIG. 8 is a side view of yet another embodiment of the catheter in accordance with the present invention.

FIG. 8 is a view of yet another embodiment of a catheter 350 in accordance with the present invention. Catheter 350 includes an elongate shaft 356. Shaft 356 includes an outer shaft 358 having a proximal end and a distal end and defining a drive shaft lumen therethrough. Shaft 356 also includes a drive shaft 360 disposed through the drive shaft lumen. A cone-shaped bearing 365 is preferably disposed at the distal end of shaft 358. Bearing 356 has a lumen extending longitudinally therethrough, and having a diameter which generally increases distally. A burr 366 is disposed at the distal end of drive shaft 360. Burr 366 can have an abrasive coating (not shown). Burr 366 is preferably formed from a plurality of spring members 380 joined at their respective proximal and distal ends. Members 380 are preferably preformed to assume a transversely expanded shape when unconstrained. The diameter of burr 366 can be reduced by withdrawing burr 366 at least in part into bearing 365. Burr 366 may be withdrawn at least partially into bearing 365 by shifting drive shaft 360 proximally relative to outer shaft 358. Burr 366 can be advanced to the cite of a lesion in the constrained configuration and then expanded, and rotated to abrade plaque.

Figure 9:
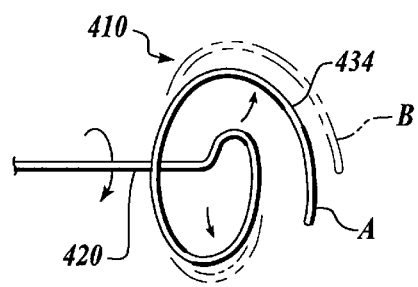
FIG. 9 is a perspective view of yet another embodiment of the catheter in accordance with the present invention.

FIG. 9 is an embodiment of yet another catheter 410 in accordance with the present invention. Catheter 410 includes a drive shaft 420 having a proximal end and a distal end. A generally spiral shaped ablation burr 434 is disposed at the distal end of drive shaft 420. Burr 434 can include an abrasive coating (not shown). Upon rotation of drive shaft 420, burr 434 can generally expand or unwind from a position A to a position B under the influence of centrifugal force. Burr 434 as shown has a generally circular cross section. Burr 434 can have a generally rectangular cross section if burr 434 were formed from a ribbon shaped member.

Figure 10:
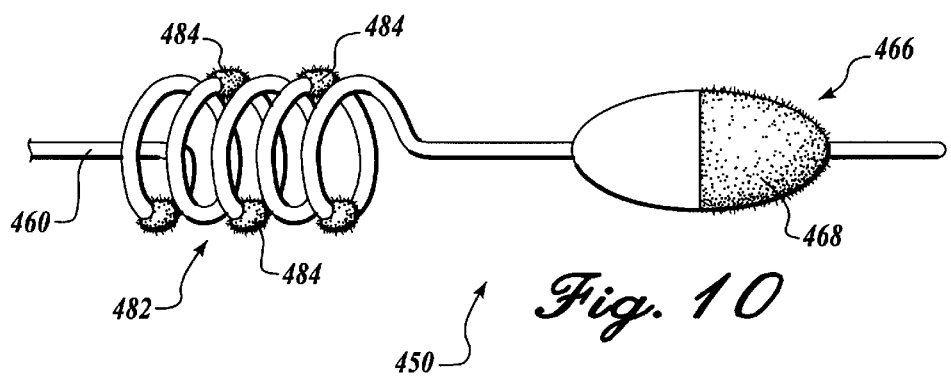
FIG. 10 is a perspective view of yet another embodiment of the catheter in accordance with the present invention.

FIG. 10 is a view of yet another embodiment of a catheter 450 in accordance with the present invention. Catheter 450 includes an elongate drive shaft 460 having a proximal end and a distal end. A burr 466 is disposed proximate the distal end of shaft 460. Burr 466 can include an abrasive coating 468. A coil 482 can be formed in drive shaft 460 proximate burr 466. Abrasive coating 484 can be deposited on coil 482. Abrasive coating 484 can be deposited in the configuration and plurality of burrs. Coil 482 can be stretched and flattened to be advanced through a guide catheter. As the coil portion of drive shaft 460 is advanced distally from a guide catheter, that portion of drive shaft 460 resumes the coil shape shown in FIG. 10.

Figure 11:
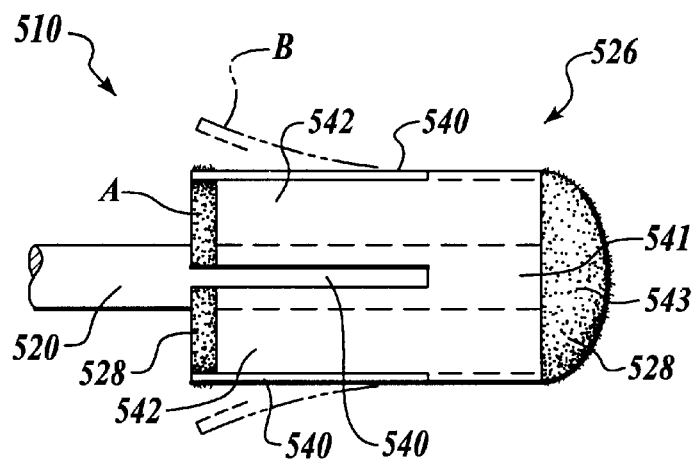
FIG. 11 is a side view of yet another embodiment of the catheter in accordance with the present invention.

FIG. 11 is a view of yet another catheter 510 in accordance with the present invention. Catheter 510 includes drive shaft 520 having a proximal end and a distal end. A burr 526 is disposed at the distal end of drive shaft 520. Burr 526 preferably includes an abrasive coating 528. Burr 526 is preferably formed from a generally tubular member 541 which is sealed at its distal end to form an abrasive tip 543. Longitudinal slits 540 are formed in the proximal end of tubular member 541 such that leaves 542 are disposed therebetween. When burr 526 is rotated, leaves 542 will move from a first position A to a second position B under the influence of centrifugal force.

Figure 12:
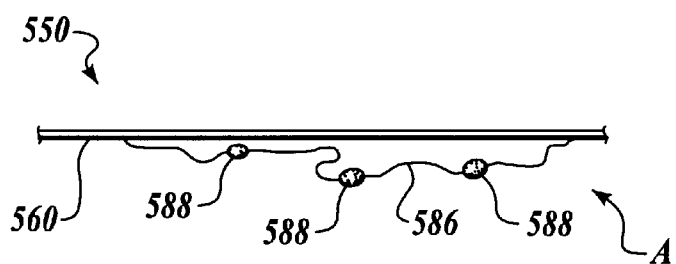
FIG. 12 is a side view of yet another embodiment of the catheter in accordance with the present invention.
Figure 13:
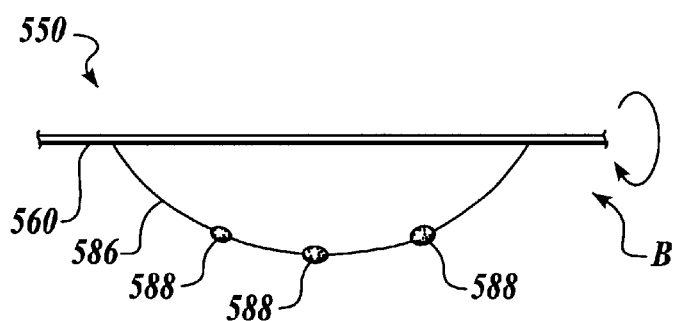
FIG. 13 is a view of the embodiment of FIG. 12 in use.

FIG. 12 is a view of yet another embodiment of a catheter 550 in accordance with the present invention. Catheter 550 includes an elongate drive shaft 560 having a proximal end and a distal end. Proximate the distal end of drive shaft 560 is a line 586 having a proximal end and a distal end. The proximal end and distal ends of line 586 are connected to drive shaft 560 at a spaced distance less than the length of line 586. Abrasive burrs 588 are deposited along line 586. In FIG. 12, line 586 is in a first position A. In FIG. 13, line 586 is shown in a second position B wherein line 586 is shift transversely under the influence of centrifugal force as drive shaft 560 is rotated.

Figure 14:
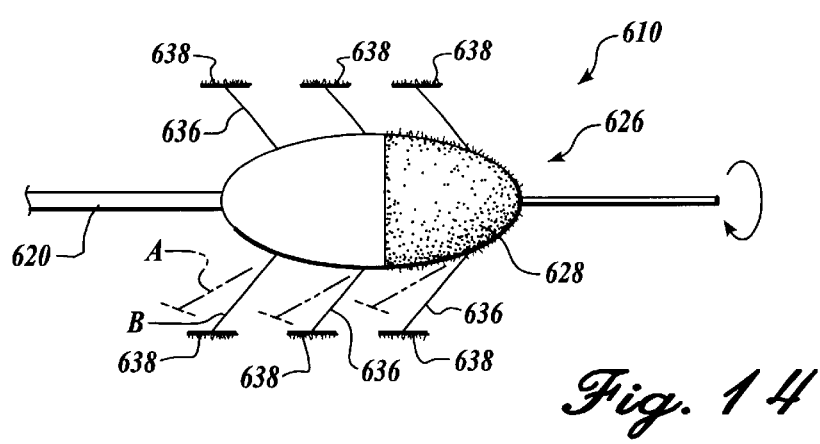
FIG. 14 is a side view of yet another embodiment of the catheter in accordance with the present invention.

FIG. 14 is a view of yet another catheter 610 in accordance with the present invention. Catheter 610 includes a drive shaft 620 having a proximal end and a distal end. A burr 626 is disposed proximate the distal end of shaft 620. Burr 626 preferably includes an abrasive coating 628. A plurality of bristles extend from burr 626. Disposed at the outside end of each bristle 636 is a burr end 638 which may include an abrasive coating. Bristles 636 can be configured to move from first position A to second position B under the influence of centrifugal force as burr 626 is rotated.

Alternately, bristles 633 may be biased to expand between positions A and B upon becoming unconstrained as they are advanced from a guide catheter.

Figures 15, 16:
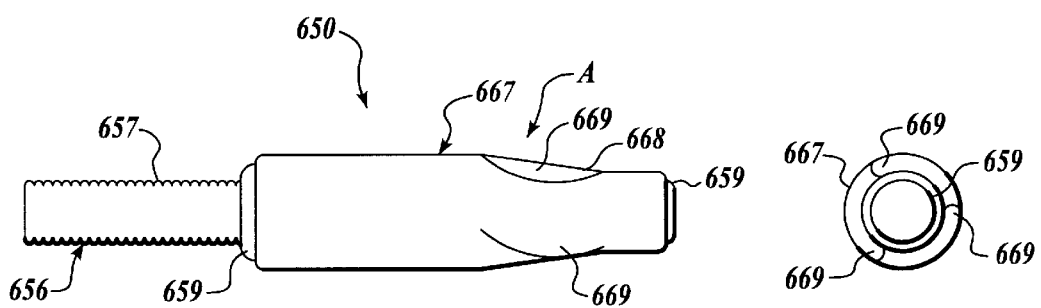
FIG. 15 is a side view of yet another embodiment of the catheter in accordance with the present invention.
FIG. 16 is a distal end view of the catheter of FIG. 15.

FIG. 15 is a side view of yet another catheter 650 in accordance with the present invention. Catheter 650 includes an elongate drive shaft 656 which can include a proximal, helical shaft encased in a polymer. Shaft 656 can also include a distal shaft portion 659 around which is disposed an elastomeric balloon 667. Elastomeric balloon 667 includes a distal portion which is folded over into folds or leaflets 669. The distal end of catheter 650 including the folded region of balloon 667 is preferably coated with an abrasive. FIG. 16 is a view of the distal end of catheter 650 of FIG. 15 and offers an alternate view of folds 669.

Figure 17:
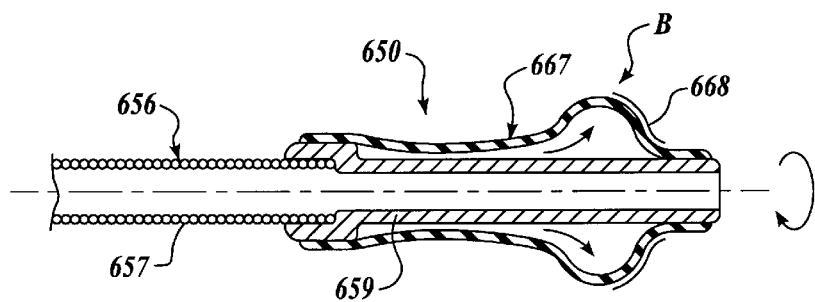
FIG. 17 is a cross-sectional view of the catheter of FIG. 15.

FIG. 17 is a cross-sectional view of catheter 650 of FIG. 15. The arrow to the right of the figure shows the direction of rotation of balloon 667. In use, as can be seen by comparison of FIG. 17 with FIG. 15, during rotation of balloon 667, the balloon's distal portion including leaves 669 expands from a first position A to a second position B. This is made possible as the space defined between the balloon inner surface and shaft 659 is preferably preloaded with a fluid such as saline prior to advancement to the site of the lesion. The quantity of fluid preloaded into balloon 667 is such that when balloon 667 is not rotated, it will be in a relatively reduced diameter, i.e., position A. Whereas, when balloon 667 is rotated, the fluid with shift by centrifugal force into that distal portion of balloon 667 including leaves 669, expanding balloon 667 into the increased diameter configuration of position B.

Figure 18:
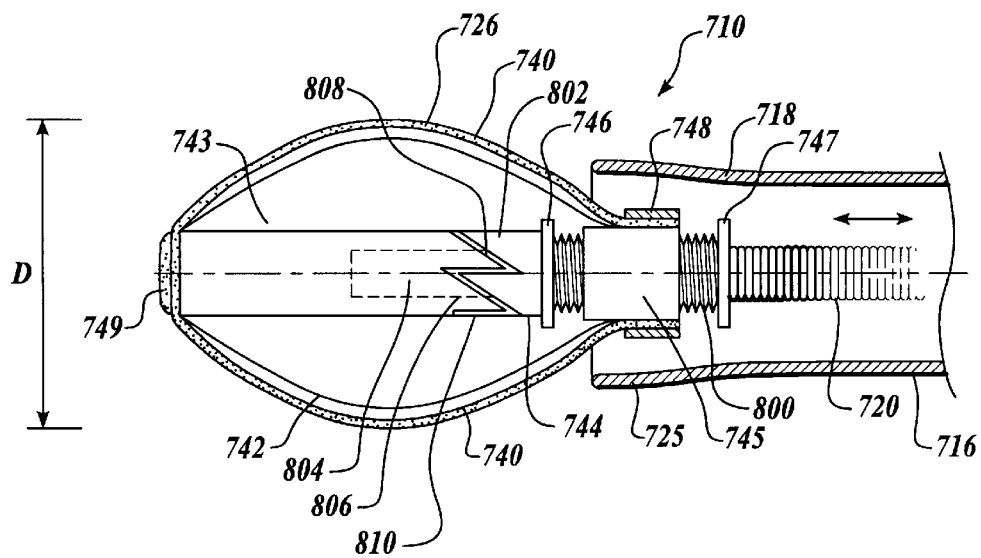
FIG. 18 is a side view of yet another embodiment of the catheter in accordance with the present invention.

FIG. 18 shows yet another alternate embodiment of a catheter 710 in accordance with the present invention. Catheter 710 has an elongate shaft 716 having a proximal end a distal end. Shaft 716 includes an outer sheath 718 defining a drive shaft lumen therethrough. Shaft 716 includes an elongate drive shaft 720 disposed through the lumen. Sheath 718 includes a distal bearing surface which preferably defines a lumen having an inside diameter increasing distally. Disposed at the distal end of drive shaft 720 is an expandable burr 726 which preferably has an abrasive coating (not shown). Burr 726 can be formed from a plurality of spring member similar to the spring members 380 of catheter 350 shown in FIG. 8. For clarity, in FIG. 18, only two spring members 740 are shown.

An elastomeric shell is disposed within burr 726 to avoid an increase in hemolysis or platelet aggregation. Shell 742 preferably encloses a main body 743 and unidirectional ratchet 744 including reverse positive stop 746. A threaded member 800 is threaded into a sleeve 745. Threaded member 800 is fixably connected at its distal end to stop 746 and fixably connected at its proximal end to forward motion positive stop 747. Threaded member 800 is also fixably connected to drive shaft 720. Spring members 740 are connected at their proximal ends to sleeve 745 and fixably held in position by collar 748. The distal ends of spring members 740 are fixably connected to the distal end of main body 743. Main body 743 is connected at its proximal end about a pin 804 to ratchet 744. Ratchet 744 includes teeth 802 and the main body portion includes teeth 806. Teeth 802 and 806 are shown in FIG. 8 meshed along angled surfaces 808 and longitudinally extended surfaces 810.

In use, ratchet 744 and main body 743 can be used to control the transverse diameter D of burr 726. For example, a burr advancable through an 8F guide catheter could be expanded between 2.0 mm and 3.5 mm in diameter, at 0.25 mm intervals or steps. The ability to control the diameter of burrs 726 at such steps can be considered indexing. To increase the diameter of burr 726 by indexing, drive shaft 720 can be rotated such that teeth 802 and 806 engage each other along surfaces 808. Since surfaces 808 are inclined, teeth 806 will tend to rise out from between 802 momentarily increasing the length of burr 726. As drive shaft 720 continues to rotate, the teeth will index and reengage the adjacent teeth. As ratchet 744 was rotated, stop 746 will have moved toward stay 745 shortening the distance between distal end 749 of burr 726 and sleeve 745, thus increasing the diameter of burr 726. This assumes that the spring members 740 bias burr 726 toward its largest diameter. This procedure can be repeated to step wise increase the diameter of burr 726. It can be appreciated that burr 726 can be kept from rotating during indexing by engagement with sheath 718 or the vessel or vessel lesion. When drive shaft 720 is rotating in the opposite direction to engage teeth 802 and 806 along longitudinally extending surface 810, burr 726 can be rotated to ablate a lesion.

The diameter of burr 726 can be reduced by merely withdrawing it at least in part into sheath 718. Burr 726 can be withdrawn into sheath 718 sufficiently such that teeth 802 and 806 will be unmeshed. When teeth 802 and 806 are unmeshed, drive shaft 720 can be rotated to advance stop 747 to sleeve 745. At that point, burr 726 is reset to index from its smallest indexing diameter to its largest as described above.

Figure 19:
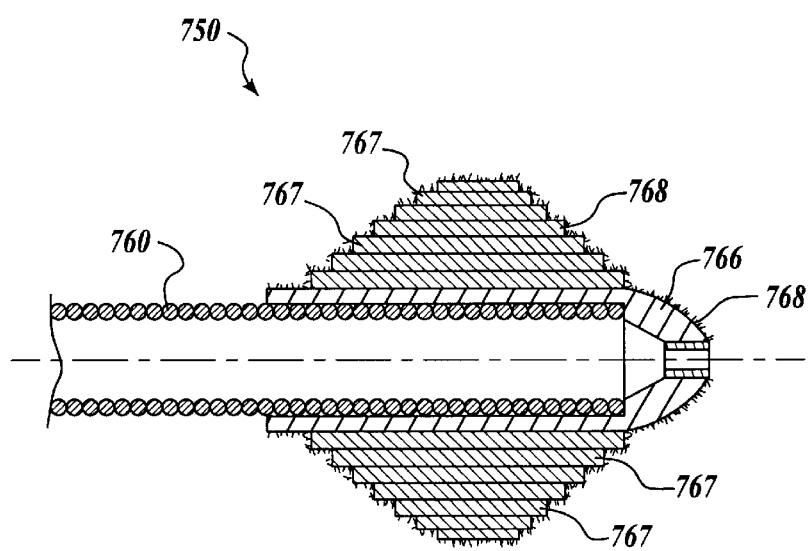
FIG. 19 is a cross-sectional view of yet another embodiment of the catheter in accordance with the present invention.

FIG. 19 is a cross-sectional view of yet another embodiment of a catheter 750 in accordance with the present invention. Catheter 750 includes an elongate drive shaft 760 having a proximal end and a distal end. Drive shaft 760 can be, for example, formed from a helical member surrounded by a polymer sheath. A burr 766 is disposed at the distal end of shaft 760 connected to burr 766 is a loosely spiraled ribbon member 767 which has a reduced length and width as it spirals outwardly from shaft 760. Abrasive coating 768 can also be applied to ribbon member 767. Like the spiraling member 434 of catheter 410 of FIG. 9, ribbon member 767 will tend to unwind and expand transversely when rotated in one direction.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A catheter assembly, comprising:
   an elongate shaft having a proximal end and a distal end, the shaft defining a lumen;
   an elongate drive shaft extending through the lumen, the drive shaft having a proximal end and a distal end;
   a burr disposed at the distal end of the drive shaft;
   a bushing disposed around the drive shaft proximate the burr that engages the burr and directs the burr within a vessel, and
   a steering line having a proximal end and a distal end, the distal end being connected to the bushing.

2. A catheter assembly in accordance with claim 1, further comprising a second steering line.

3. The catheter assembly in accordance with claim 1, wherein the burr includes an abrasive surface.

4. The catheter assembly of claim 1, wherein the bushing and the burr are rotatably coupled.

5. A method of removing deposits from a vascular lumen, comprising:

inserting a catheter having a proximal end, a distal end, and one or more lumens extending therethrough into a vascular lumen;

inserting an atherectomy device through a lumen in the catheter, the atherectomy device having a tissue removal burr, a driveshaft that rotates the tissue removal burr, and a bushing that is proximal to the tissue removal burr; and urging the bushing against the tissue removal burr as the burr is being rotated by the drive shaft to deflect the burr and selectively engage and remove deposits in the vascular lumen.

6. The method of claim 4, wherein the bushing is urged against the burr by manipulating one or more steering wires coupled to the bushing.

* * * * *

UNITED STATES PATENT AND TRADEMARK OFFICE
CERTIFICATE OF CORRECTION

PATENT NO. : 6,596,005 B1
DATED : July 22, 2003
INVENTOR(S) : D. Drummond et al.

It is certified that error appears in the above-identified patent and that said Letters Patent is hereby corrected as shown below:

Title page,
Item [12], "Kanz et al." should read -- Drummond et al. --
Item [75], Inventors, Bill Kanz, Sacramento, CA (US); Denise Drummond, North Ogden, UT (US); Robert Barry, Kirkland, WA (US); Paul A. Hirst, Liberty Lake, WA (US); Mark Wyzgala, Bellevue, WA (US); Gary Swinford, Issaquah, WA (US); Edward Wulfman, Woodinville, WA (US); Tom Clement, Redmond, WA (US); Tom Kadavy, Bellevue, WA (US)" should read -- Denise Drummond, North Ogden, UT (US); Robert Barry, Kirkland, WA (US) --

Column 12,
Line 6, "claim 4," should read -- claim 5, --

Signed and Sealed this

Twenty-fourth Day of February, 2004

JON W. DUDAS
*Acting Director of the United States Patent and Trademark Office*